United States Patent [19]
Hauck et al.

[11] 3,965,102
[45] June 22, 1976

[54] 1,2,3,4,6,7,8,8A-OCTAHYDRO-6-ARYL-ISOQUINOLINES AND DERIVATIVES THEREOF

[75] Inventors: Frederic Peter Hauck, Somerville, N.J.; Joseph E. Sundeen, Yardley, Pa.

[73] Assignee: E. R. Squibb & Sons, Inc., Princeton, N.J.

[22] Filed: Oct. 4, 1974

[21] Appl. No.: 512,277

Related U.S. Application Data

[63] Continuation-in-part of Ser. No. 295,386, Oct. 5, 1972, abandoned.

[52] U.S. Cl. .................. 260/286 R; 260/287 CF; 260/240 D; 260/287 D; 424/258
[51] Int. Cl.² .............. C07D 217/04; C07D 491/04
[58] Field of Search ......... 260/287 R, 346.6, 287 D, 260/286 R

[56] References Cited
UNITED STATES PATENTS

| | | | |
|---|---|---|---|
| 2,264,429 | 12/1941 | Bergmann | 260/346.6 |
| 2,359,038 | 9/1944 | Hopff | 260/346.6 |
| 2,506,654 | 5/1950 | Stein | 260/287 R |
| 3,156,695 | 11/1964 | Stein | 260/287 G |
| 3,410,876 | 11/1968 | DiLeone | 260/346.6 |
| 3,609,123 | 9/1971 | Rabilloud | 260/287 R |

OTHER PUBLICATIONS

Gautier, "PhD. Thesis" University of New Hampshire, 1966, pp. 116–117, 135.

*Primary Examiner*—Alton D. Rollins
*Assistant Examiner*—David E. Wheeler
*Attorney, Agent, or Firm*—Lawrence S. Levinson; Merle J. Smith; Stephen B. Davis

[57] ABSTRACT

1,2,3,4,6,7,8,8a-Octahydro-6-phenyl or substituted phenyl-isoquinolines and derivatives thereof and their methods of preparation are disclosed. These compounds are useful as anti-inflammatory agents.

7 Claims, No Drawings

1,2,3,4,6,7,8,8A-OCTAHYDRO-6-ARYL-ISOQUINOLINES AND DERIVATIVES THEREOF

This application is a continuation-in-part of Ser. No. 295,386 filed in Oct. 5, 1972, now abandoned.

This invention is directed to compounds of the formula

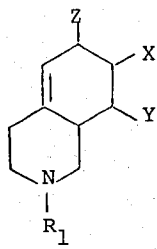

IV wherein Z is phenyl of substituted phenyl; $R_1$ is hydrogen, lower alkyl, or phenyl-lower alkyl; and X and Y are both —COOH, $$-\overset{O}{\underset{\|}{C}}-O-\text{lower alkyl}, -CH_2OH, \text{ or } -CH_2-O-\overset{O}{\underset{\|}{C}}-\text{lower alkyl}$$

and the pharmaceutically acceptable acid addition salts thereof.

Also within the scope of this invention are the following compounds wherein Z and $R_1$ are as defined above

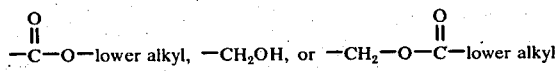

I    II    III

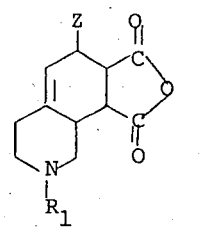

IVa which are useful as intermediates in the preparation of the compounds of formula IV.

The term substituted phenyl is intended to encompass one or two substituents which may be alike or different and which are selected from the group consisting of lower alkyl, lower alkoxy, nitro, halogen, trifluoromethyl, cyano, carbo-lower alkoxy, and carboxy.

The term lower alkyl is intended to mean a straight or branched chain alkyl group of from one to eight carbon atoms.

The term lower alkoxy is intended to mean a straight or branched chain alkyl group of from one to eight carbon atoms linked directly to an oxygen atom.

The compounds of the present invention may exist in a number of optical or geometric isomeric forms such as steroisomeric forms, endo and exo forms, etc. All of these optical and geometric isomers are intended to be within the scope of the present invention. Position isomers of the compounds of formula IV are disclosed in copending application Ser. No. 295,385 filed on Oct. 5, 1972, now U.S. Pat. No. 3,901,897.

The preferred compounds of formula IV are those wherein $R_1$ is methyl or benzyl especially methyl; X and Y are both carboxyl or hydroxymethyl; and Z is phenyl or methoxyphenyl.

The compounds of this invention may be prepared by reacting 4-picoline with a substituted benzaldehyde

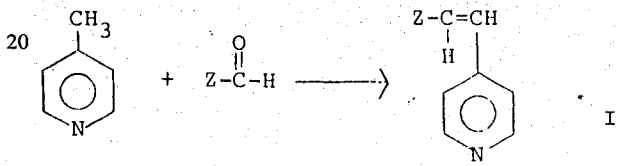

I to yield the intermediate of formula I. The compound of formula I is then reacted with a halide and reduced to yield the intermediate

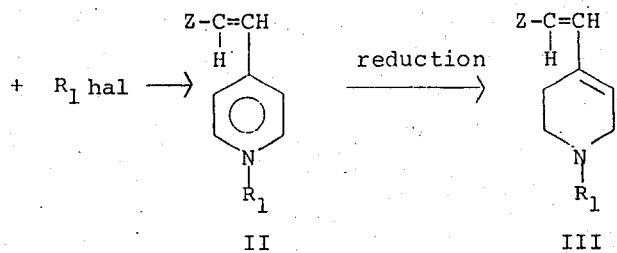

of formula III. This sequence of reactions is disclosed in the Ph.D. Thesis of George Gautier (University of New Hampshire, 1966).

Gautier reports the ability of an intermediate of formula III to react with the dienophile N-phenylmaleimide to give the Diels-Alder Adduct. However, this same thesis reports the inability of maleic anhydride to react with a compound of formula III. Since maleic anhydride and N-phenylmaleimide are two of the most reactive dienophiles, the ability of compounds of formula III to part take in the Diels-Alder Reaction on a broad basis and not in just one isolated case seemed very much in question.

This invention teaches the procedures enabling one to react compounds of formula III with maleic anhydride and obtain the desired Diels-Alder Adduct.

It has been found that the intermediate of formula III will react with an acidic dienophile such as maleic anhydride only when the compounds of formula III are reacted in the form of a salt of a strong acid. Thus, the reaction of maleic anhydride wth the hydrochloride of formula III gives the desired Diels-Alder Adduct IVa.

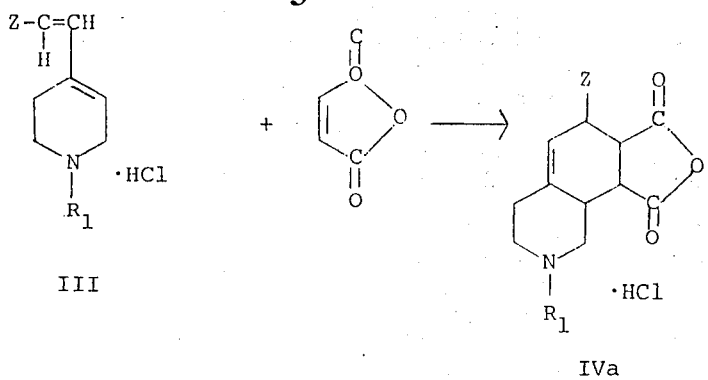

The reaction of the salt of formula III and the dienophile are generally carried out in a lower alkanoic acid-lower alkanoic acid anhydride mixture, such as acetic acid - acetic anhydride, butyric acid - butyric anhydride, acetic acid - propionic anhydride, etc. at a temperature range of from about 75° to about 175°C, preferably 120° to 140°C. Reaction rates very considerably; however, the reactions can be followed by way of thin film chromatography and are continued until completion which is usually within a 24 hour period.

The dienes are used in the form of a salt of a strong acid and the aminO group must also be trisubstituted. Some typical examples of dienes which may be employed in the process of this invention are 1-methyl-4-styryl-1,2,5,6-tetrahydropyridine and 1-benzyl-4-p-methoxystyryl-1,2,5,6-tetrahydropyridine.

The maleic anhydride Diels-Alder Adduct intermediate of of formula IVa when reduced with lithium aluminum hydride gives the corresponding alcohol (Gaylord, "Reductions with Complex Metal Hydrides" or Organic Reactions, VI, p. 469, Wiley). This alcohol may be converted to the corresponding ester by reaction with an anhydride [(alkylCO)$_2$O] in pyridine (Shriner and Fuson, "Identifications of Organic Compounds" p. 165 and 177).

The intermediate of formula IVa may be reacted with water or an alcohol depending upon reaction conditions to give a dicarboxylic acid (water and heat) or a diester (alcohol, HCl, and heat) (Rodd, "Chemistry of Carbon Compounds", Vol. IB, p. 974, Elsevier). Reduction of the diester with lithium aluminum hydride will give the corresponding alcohol.

In carrying out the initial process of this invention, a tertiary amine is employed. In order to obtain the useful sceondary amines or compounds which are readily prepared from secondary amines, a tertiary benzyl amine is employed in the Diels-Alder Reaction and removed by utilizing a catalytic amount of palladium on charcoal in an organic solvent such as ethanol in the presence of hydrogen. This reaction is of special interest, since one would expect the double bond to be reduced simultaneously; however, such is not the case and high yields of debenzylated olefin is obtained.

The resultant secondary amines are converted to other useful tertiary amines by alkylation using alkylating agents such as dimethyl sulfate, methyl iodide, etc. or amides by acylation using acylating agents such as acetyl chloride, propionic anhydride, etc.

The compounds of formula IV and their pharmaceutically acceptable acid addition salts are useful as antiinflammatory agents in mammals, such as cattle, dogs, sheep, etc. when administered in amounts ranging from about 0.3 mg to about 15 mg per kg of body weight per day. A preferred dosage regimen for optimum results would be from about 0.6 mg to about 10 mg per kg of body weight per day, and such dosage units are employed that a total of from about 20 mg to about 280 mg of active ingredient for a subject of about 70 kg body weight are administered in a 24 hour period preferably, 40 mg to 140 mg. The compounds of the present invention in the described dosages are intended to be administered orally; however, other routes such as rectally, intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

1,2,3,6-Tetrahydro-4-(p-methoxystyryl)-1-methylpyridine, hydrochloride a. A mixture of 4-picoline (280 g, 3.0 moles), p-methoxybenzaldehyde (410 g, 3.0 moles), and 500 ml. of acetic anhydride is refluxed for 24 hours, cooled, evaporated in vacuo, and the residue taken up in water and basified with 10% NaOH. The solid is filtered and crystallized from ethanol and water to give 350 g (55%) of the crude base. Recrystallization gives pure 4-(p-methoxystyryl)-pyridine, mp 128°–130°.

b. The crude 4-(p-methoxystyryl)-pyridine (160 g, 0.76 mole) in 300 ml. acetonitrile is heated to effect solution, then treated with 100 ml. (2.3 moles) methyl iodide, in portions. The mixture is refluxed on steam bath for 1 hour, then cooled to afford 210 g (87% of crystalline methiodide.

c. A solution of 100 g (0.31 mole) of the methiodide in 800 ml. of aqueous methanol is treated at 40°C (cooling) with 22 g of sodium borohydride, in portions, then stirred at 35°C for 2 hours. The mixture is cooled and extracted with ether. The dried ($K_2CO_3$) extract is evaporated to give 60 g of crude diene amine (83%).

d. The free base (60 g) is taken up in 1 liter of isopropanol and treated with HCl in isopropanol in excess. After 16 hours at 0°C, ether is added to complete crystallization of the hydrochloride (53 g, 76%).

e. A 10 g sample of the crude hydrochloride is recrystallized from isopropanol, then from isopropanol-methanol to give 6.4 g of the analytical sample, mp 219°–221°C.

EXAMPLE 2

According to the method of Example 1, if one substitutes in place of the p-methoxybenzaldehyde, an equivalent amount of o-chlorobenzaldehyde one obtains the hydrochloride of 1,2,3,6-tetrahydro-4-(o-chlorostyryl)-1-methylpyridine.

EXAMPLE 3–5

According to the method of Example 1, if one substitutes in place of the methyl iodide, the following compounds:
  ethyl iodide,
  phenethyl iodide, and
  i-propyl iodide,
one obtains:
  1,2,3,6-tetrahydro-4-(p-methoxystyryl)-1-ethylpyridine hydrochloride,
  1,2,3,6-tetrahydro-4-(p-methoxystyryl)-1-phenethylpyridine hydrochloride, and
  1,2,3,6-tetrahydro-4-(p-methoxystyryl)-1-i-propylpyridine hydrochloride, respectively.

EXAMPLE 6

1-Benzyl-1,2,3,6-tetrahydro-4-(p-methoxystyryl)-pyridine, hydrochloride a. A mixture of 4-picoline (280 g, 3.0 moles), p-methoxy benzaldehyde (410 g, 3.0 moles) and 500 ml. acetic anhydride is refluxed for 24 hours, cooled, evaporated in vacuo, and the residue taken up in water and basified with 10% sodium hydroxide. The solid is filtered and crystallized from ethanol and water to give 350 g (55%) crude 4-(p-methoxystyryl)-pyridine.

b. The crude styrene (84 g, 0.4 moles) in 1 liter of acetonitrile is heated to effect solution, then treated with 80 ml. (0.7 moles) benzyl chloride dropwise over 20 minutes. The mixture is refluxed for 3.5 hours under nitrogen and allowed to cool. The crystals are filtered (109 g) and a second crop obtained by adding ether to the filtrate (9 g, 88%).

c. The crystalline benzyl chloride salt (118 g, 0.35 moles) is dissolved in 1 liter methanol and sodium borohydride (20 g, 0.53 moles) is added in portions with stirring (T ≤ 35°C). This is stirred for 1 hour and the solid filtered. The solid is dissolved in dichloromethane, dried (potassium carbonate), and evapoated to yield 97 g (90%) of 1-benzyl-1,2,3,6-tetrahydro-4-(p-methoxystyryl)-pyridine.

d. The tetrahydrostyrene (64 g) is dissolved in 4 liters of ether and filtered. Then hydrochloric acid in isopropanol is added until the solution is acid to pH paper. The solid is recrystallized from ethanol to yield 50.5 g (72%) of the hydrochloride salt, mp 239°–254°C with decomposition.

EXAMPLE 7

1,2,3,6-Tetrahydro-1-methyl-4-styrylpyridine hydrochloride

To a cooled and stirred solution of 1,2,3,6-tetrahydro-1-methyl-4-styrylpyridine (53.6 g) prepared according to the method of Gautier (Ph. D. Thesis, University of New Hampshire, 1966 p. 134) in dry ether (300 ml.), isopropanol saturated with dry hydrochloric acid is added until precipitation was complete. The product after ether washing and recrystallization from methanol-ether is obtained in a 68 percent yield, which melts with decomposition at 289.5°–290°C.

EXAMPLE 8–9

According to the method of Example 7, if one substitutes in place of the 1,2,3,6-tetrahydro-1-methyl-4-styrylpyridine the following compounds prepared utilizing the general procedure of Gautier:
  1,2,3,6-tetrahydro-1-benzyl-4-(o-methylstyryl)-pyridine,
and
  1,2,3,6-tetrahydro-1-propyl-4-(p-trifluoromethylstyryl)-pyridine;
one obtains the corresponding hydrochloride.

EXAMPLE 10

1,2,3,4,6,7,8,8a-Octahydro-2-methyl-6-phenyl-7,8-isoquinoline-dicarboxylic acid anhydride, hydrochloride A solution of 50 g. maleic anhydride and 10 g. 1,2,3,6-tetrahydro-1-methyl-4-styrylpyridine hydrochloride, from example 7, in 100 ml. acetic acid and 100 ml. acetic anhydride previously thoroughly sparged with dry nitrogen is refluxed gently for 3 hours under nitrogen. The reaction mixture is concentrated to 100 ml. volume, and flushed with 300 ml. benzene to remove most of the remaining solvent. The residue is triturated with benzene several times to give 17.5 g. of a crude brown product. This compound is not further purified. It is refrigerated in the dry state for storage.

Similarly, by following the procedure of Example 10 but employing the products of any of examples 1 to 6, 8 or 9 other compounds within the scope of formula IVa are obtained.

EXAMPLE 11

1,2,3,4,6,7,8,8a-Octahydro-2-methyl-6-phenyl-7,8-isoquinoline dicarboxylic acid, hydrochloride, ethanol solvate (2:1), hydrate A solution of 17.5 g of the material prepared in Example 10 in 36 ml. water is removed in vacuo, and the residue is flushed with ethanol and benzene. Trituration of the residue with ice cold ethanol gives 8.5 g of a colorless crystalline product dried in vacuo at room temperature. Two crystallizations from 95% ethanol give the named product, mp after drying 1.5 hours at 100°: 228°–235° with decomposition, VPC and NMR indicated the presence of ½ mole ethanol of crystallization. Karl Fischer analysis confirmed 1 mole water of crystallization. The mass spectrum confirmed the molecular weight.

EXAMPLE 12

1,2,3,4,6,7,8,8a-Octahydro-6-(p-methoxyphenyl)-2-methyl-7,8-isoquinolinedicarboxylic acid, hydrochloride 10 g (0.0275 moles) of 1,2,3,4,6,8,8a-Octahydro-6-(p-methoxyphenyl)-2-methyl-7,8-isoqinolinedicarboxylic acid anhydride hydrochloride (prepared according to the procedure of example 10) is treated with 100 ml. of water on a steam bath for ½ hour. The solution is allowed to cool for ½ hour and evaporated The tacky solid is treated with isopropyl alcohol to precipitate a granular solid which upon recrystallization from methanol-ether yields 9.6 g (82%), 1,2,3,4,6,7,8,8a-octahydro-6-(p-methoxyphenyl)-2-methyl-7,8-isoquinolinedicarboxylic acid, hydrochloride. Further recrystallization gives a product which melts with decomposition at from 210° to 236°C.

EXAMPLES 13 – 15

According to the method of Example 12, if one employs the following compounds (prepared according to the procedure of example 10):
2-benzyl-1,2,3,4,6,7,8,8a-octahydro-6-(p-methoxyphenyl)-7,8-isoquinoline dicarboxylic anhydride, hydrochloride,
2-propyl-1,2,3,4,6,7,8,8a-octahydro-6-(m-nitrophenyl)-7,8-isoquinoline dicaboxylic anhydride, hydrochloride, and 2-methyl-1,2,3,4,6,7,8,8a-octahydro-6-(o-cyanophenyl)-7,8-isoquinoline dicarboxylic anhydride, hydrochloride,
one obtains the corresponding dicarboxylic acids.

EXAMPLE 16

2-Benzyl-1,2,3,4,6,7,8,8a-octahydro-6-(p-methoxyphenyl)-7,8-isoquinolinedicarboxylic acid, dimethyl ester, hydrochloride A solution of 21 g (0.06 moles) 1-benzyl-1,2,3,6-tetrahydro-4-(p-methoxystyryl)-pyridine, hydrochloride, from example 6, 37.8 g ground maleic anhydride, 135 ml. glacial acetic acid, 135 ml. acetic anhydride and 20 mg hydroquinone is refluxed under nitrogen for ½ hour. The solution is allowed to cool and evaporate to an oil. The crude Diels-Alder adduct (quantitative yield of 2-benzyl-1,2,3,4,6,7,8,8a-octahydro-6-(p-methoxyphenyl)-7,8-isoquinoline-dicarboxylic acid anhydride hydrochloride) is dissolved in 500 ml. methanol and 20 ml. hydrochloric acid in isopropanol and refluxed for 18 hours. The solution is allowed to cool and evaporated. The residue is triturated in ether and solid filtered to afford a quantitative yield of 2-benzyl-1,2,3,4,6,7,8,8a-octahydro-6-(p-methoxyphenyl)-7,8-isoquinoline-dicarboxylic acid, dimethyl ester, hydrochloride. After recrystallization from acetone-ether the mp is 200° to 209°C with decomposition.

EXAMPLES 17 – 19

According to the method of Example 16, if one substitutes in place of the 1-benzyl-1,2,3,6-tetrahydro-4-(p-methoxystyryl)-pyridine, hydrochloride the appropriate diene one obtains the following compounds:
2-methyl-1,2,3,4,6,7,8,8a-octahydro-6-phenyl-7,8-isoquinoline-dicarboxylic acid, dimethyl ester, hydrochloride,
2-pentyl-1,2,3,4,6,7,8,8a-octahydro-6-(m-nitrophenyl)-7,8-isoquinolinedicarboxylic acid, dimethyl ester, hydrochloride, and
2-methyl-1,2,3,4,6,7,8,8a-octahydro-6-(p-carboxyphenyl)-7,8-isoquinolinedicarboxylic acid, dimethyl ester, hydrochloride.

EXAMPLE 20

1,2,3,4,6,7,8,8a-Octahydro-2-methyl-6-phenyl-7,8-isoquinolinedimethanol

To 50 g lithium aluminum hydride in 100 ml. dry ether with rapid stirring under nitrogen is added with ice bath cooling 360 ml. dioxane. The resulting slurry is refluxed gently and 48.7 g of 1,2,3,4,6,7,8,8a-octahydro-2-methyl-6-phenyl-7,8-isoquinoline dicarboxylic anhydride hydrochloride is added in portions over 1 hour such as to control foaming and to maintain a gentle reflux rate (No external heating was necessary during this period). The resulting slurry was refluxed for 22 hours. With occasional cooling, sufficient saturated aqueous potassium carbonate is added (cautiously) to decolorize the slurry (about 350 ml). The slurry is filtered, and the filtrate, combined with 2 benzene washes, gives on concentration in vacuo 12 g wet colorless oil. The product was crystallized from benzene/pet ether to give 7.0 g of crystalline material. Successive washings of the filter cake with methylene chloride and then exhaustively with hot dioxane-ether give an additional 11.4 g amber colored material. (44%) Recrystallization from benzene/pet ether and then from acetone yield 4.5 g pure amino diol mp 153°–155° plus an additional 7.7 g (27%).

EXAMPLE 21

1,2,3,4,6,7,8,8a-Octahydro-6-(p-methoxyphenyl)-2-methyl-7,8-isoquinolinedimethanol To a slurry of 15 g lithium aluminum hydride in 800 ml. ether and 400 ml. dioxane is added 15 g (0.041 moles) 1,2,3,4,6,7,8,8a-octahydro-6-(p-methoxyphenyl)-2-methyl-7,8-isoquinoline-dicarboxylic acid anhydride hydrochloride slowly with stirring under nitrogen. This mixture is refluxed ovenight. Saturated potassium carbonate solution is added until the solution is white. This is filtered and washed with hot dioxane. The organics are combined and evaporated to yield 7.9 g (61%) crude 1,2,3,4,6,7,8,8a-octahydro-6-(p-methoxyphenyl)-2-methyl-7,8-isoquinolinedimethanol. The oil is crystallized from ethyl acetate, and recrystallization of 2 g from ethyl acetate gives an analytical sample, 1.7 g, mp 169°–171°C.

EXAMPLE 22

2-Benzyl-1,2,3,4,6,7,8,8a-octahydro-6-(p-methoxyphenyl)-7,8-isoquinolinedimethanol A solution of 87 g (0.19 moles) of dimethyl 1,2,3,4,6,7,8,8a-octahydro-2-benzyl-6-(p-methoxyphenyl)-7,8-isoquinolinedicarboxylate in 800 ml. ether is added dropwise to a slurry of 14.3 g (0.39 moles) lithium aluminum hydride in 600 ml. ether with stirring under nitrogen. This is refluxed for 1.5 hours and allowed to stir overnight at room temperature. A saturated sodium carbonate solution is added until the mixture is white. The salts are filtered and washed with ether. Evaporation of the filtrates yields 50 g crude diol. The salts are washed with dichloromethane and filtered. Evaporation of these filtrates yields 3.2 g crystalline diol. The salts are boiled in dioxane and filtered. Evaporation of the dioxane yields about 23 g crude diol. Crystallization of the crude diol from the ether filtrates from ethyl acetate yields about 17 g 2-benzyl-1,2,3,4,6,7,8,8a-octahydro-6-(p-methoxyphenyl)-7,8-isoquinolinedimethanol. Recrystallization of 2.5 g from ethyl acetate-methanol affords an analytically pure sample, 1,3 g, mp 145°–147°C.

EXAMPLES 23 and 24

According to the method of Example 22, if one substitutes in place of the dimethyl 1,2,3,4,6,7,8,8a-octahydro-2-benzyl-6-(p-methoxyphenyl)-7,8-isoquinolinedicarboxylate, the following compounds:
diethyl 1,2,3,4,6,7,8,8a-octahydro-2-benzyl-6-(m-i-propylphenyl)-7,8-isoquinolinedicarboxylate, and
dimethyl 1,2,3,4,6,7,8,8a-octahydro-2-methyl-6(o-methylphenyl)-7,8-isoquinolinedicarboxylate,
one obtains:
1,2,3,4,6,7,8,8a-octahydro-2-benzyl-6-(m-i-propylphenyl)-7,8-isoquinolinedicarboxylate, and
1,2,3,4,6,7,8,8a-octahydro-2-methyl-6-(o-methylphenyl)-7,8-isoquinolinedicarboxylate.

EXAMPLE 25

1,2,3,4,6,7,8,8a-Octahydro-2-methyl-6-phenyl-7,8-isoquinolinedimethanol, diacetate ester To 5.7 g of 1,2,3,4,6,7,8,8a-octahydro-2-methyl-6-phenyl-7,8-isoquinolinedimethanol in 50 ml, dry pyridine-acetic anhydride (25 ml) is added with cooling in an ice bath slowly. After 1 hour in an ice bath the resulting solution is kept at room temperature 22 hours. Most of the solvent mixture is removed in vacuo. A methylene chloride solution of the residue is washed exhaustively with aqueous sodium bicarbonate and then with water, dried over magnesium sulfate and concentrated in vacuo to give 7.3 g residue after flushing twice with benzene and once with acetone (pyridine odor nearly absent). Trituration with benzene/pet ether gives 7.0 g of crystalline product in 3 crops. Recrystallization from hot hexane affords about 4.14 g (64%) of pure product, mp 100°–103.5°.

EXAMPLE 26

2-Benzyl-1,2,3,4,6,7,8,8a-octahydro-6-(p-methoxyphenyl)-7,8-isoquinolinedimethanol, diacetate ester, hydrochloride To a solution of 5.4 g (0.013 moles) of 2-benzyl-1,2,3,4,6,7,8,8a-octahydro-6-(p-methoxyphenyl)-7,8-isoquinoline dimethanol in 100 ml. pyridine, 50 ml. acetic anhydride is added dropwise. This is stirred overnight at room temperature. After stirring for an additional 16 hours, the solution is evaporated. The residue is dissolved in ether and stirred with saturated sodium bicarbonate solution for ½ hour. The layers are separated and the aqueous is extracted with ether. The organic layers are dried (magnesium sulfate) and evaporated to yield 4.6 g diacetate ester. Column chromatography (basic alumina, Activity II, in chloroform) yields about 4.4 g pure 2-benzyl-1,2,3,4,6,7,8,8a-octahydro-6-(p-methoxyphenyl)-7,8-isoquinolinedimethanol, diacetate ester. This is dissolved in ether and hydrochloric acid in isopropanol-ether is added until the solution is acidic to pH paper. The solid is filtered and recrystallized from acetone-ether and is isopropanol-ether to yield 4.6 g (65%) hydrochloride. Recrystallization of 3 g from isopropanol-ether affords an analytical sample, 0.9 g, mp 171°–173°C.

EXAMPLES 27 – 29

According to the method of Example 26, if the substitutes in place of the acetic anhydride the following compounds:
i-propionic acid anhydride,
butyric acid anhydride, and
2-ethylpropionic acid anhydride,
one obtains:
2-benzyl-1,2,3,4,6,7,8,8a-octahydro-6-(p-methoxyphenyl)-7,8-isoquinolinedimethanol, di-i-propionate ester, hydrochloride,
2-benzyl-1,2,3,4,6,7,8,8a-octahydro-6-(p-methoxypehnyl)-7,8-isoquinolinedimethanol, di-butyrate ester, hydrochloride, and
2-benzyl-1,2,3,4,6,7,8,8a-octahydro-6-(p-methoxyphenyl)-7,8-isoquinolinedimethanol, di-2-ethylpropionate ester, hydrochloride, respectively.

EXAMPLE 30

1,2,3,4,6,7,8,8a-Octahydro-6-(p-methoxyphenyl)-7,8-isoquinolinedimethanol, diacetate ester, oxalate salt (1:1)

An 11 g (0.023 mole) sample of 2-benzyl-1,2,3,4,6,7,8,8a-octahydro-6-(p-methoxyphenyl)-7,8-isoquinolinedimethanol, diacetate ester, is debenzylated in 200 ml. absolute ethanol with 1 g palladium on carbon. After 4 days at 30 psi on the Parr apparatus, the sample is filtered and the catalyst is washed with ethanol. The combined filtrates are evaporated. Column chromatography (basic alumina, activity II in chloroform) yields about 4.6 g (52%) debenzylated diacetate, and 4.6 g of the starting benzyl compound A 2.3 g (0.006 mole) sample of this debenzylated material is dissolved in 10 ml. isopropanol and 0.67 g (0.005 moles) oxalic acid is next added. This is swirled and heated slightly to dissolve the acid. The addition of ether affords about 2.5 g (100%) crystalline 1,2,3,4,6,7,8,8a-octahydro-6-(p-methoxyphenyl)-7,8-isoquinolinedimethanol, diacetate ester, oxalate salt (1:1). Further recrystallization of 2.5 g from methanol-isopropanol-ether gives an analytically pure sample, 0.95 g, mp 105°–110°C.

EXAMPLES 31 and 32

According to the method of Example 30, if one substitutes in place of the 2-benzyl-1,2,3,4,6,7,8,8a-octahydro-6-(p-methoxyphenyl)-7,8-isoquinolinedimethanol, diacetate ester, the following compounds:

1,2,3,4,6,7,8,8a-octahydro-6-phenyl-7,8-isoquinolinedimethanol, dipropionate ester, and diethyl-1,2,3,4,6,7,8,8a-octahydro-6-phenyl-7,8-isoquinolinedicarboxylate, one obtains the corresponding debenzylated compound.

EXAMPLE 33

PREPARATION OF TABLET FORMULATION

| Ingredient | Milligrams per Tablet |
| --- | --- |
| 1,2,3,4,6,7,8,8a-octahydro-2-methyl-6-phenyl-7,8-isoquinolinedimethanol | 100 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120°F. The dry granules are passed through a No. 16 screen. The mixture is lubricated with magnesium stearate and compressed into tablets in a suitable tableting machine. Each tablet contains 300 milligrams of active ingredient.

EXAMPLE 34

PREPARATION OF ORAL SYRUP FORMULATION

| Ingredient | Amount |
| --- | --- |
| 1,2,3,4,6,7,8,8a-octahydro-6-(p-methoxyphenyl)-2-methyl-7,8-isoquinolinedicarboxylic acid, hydrochloride | 500 mg |
| Sorbitol solution (70% N.F.) | 40 ml |
| Sodium benzoate | 150 mg |
| Sucaryl | 90 mg |
| Saccharin | 10 mg |
| Red dye (F.D. & C. No. 2) | 10 mg |
| Cherry flavor | 50 mg |
| Distilled water    qs to | 100 ml |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. A compound of the formula

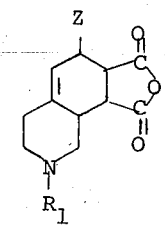

wherein Z is phenyl or methoxyphenyl; R₁ is methyl or benzyl; and a pharmaceutically acceptable salt thereof.

2. The compound of claim 1 having the name 1,2,3,4,6,7,8,8a-octahydro-2-methyl-6-phenyl-7,8-isoquinolinedicarboxylic acid anhydride, hydrochloride, 3. A compound of the formula:

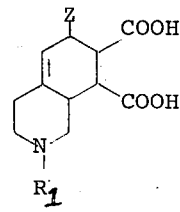

wherein Z is phenyl or methoxyphenyl; R₁ is methyl or benzyl; and a pharmaceutically acceptable acid addition salt thereof.

4. The compound having the name 2-benzyl-1,2,3,4,6,7,8,8a-octahydro-6-(p-methoxyphenyl)-7,8-isoquinoline-dicarboxylic acid, dimethyl ester, hydrochloride.

5. The compound of claim 3 having the name 1,2,3,4,6,7,8,8a-octahydro-6-(p-methoxyphenyl)-2-methyl-7,8-isoquinoline-dicarboxylic acid, hydrochloride.

6. The compound having the name 1,2,3,4,6,7,8,8a-octahydro-2-methyl-6-phenyl-7,8-isoquinolinedicarboxylic acid, dimethyl ester, hydrochloride.

7. The method of preparing the compound of claim 1 which comprises the step of reacting the hydrochloride salt of a compound of the formula

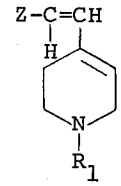

wherein z and R₁ are as defined in claim 1 with maleic anhydride in a lower alkanoic acid - lower alkanoic acid anhydride mixture at a temperature of from about 75° to about 175°C.

* * * * *

UNITED STATES PATENT AND TRADEMARK OFFICE
CERTIFICATE OF CORRECTION

PATENT NO. : 3,965,102

DATED : June 22, 1976

INVENTOR(S) : Frederic P. Hauck et al

It is certified that error appears in the above-identified patent and that said Letters Patent are hereby corrected as shown below:

Col. 1, line 6, "in" should read --on--.

Col. 1, line 22, "of" should read --or--.

Col. 2, line 66, "wth" should read --with--.

Col. 3, line 22, "very" should read --vary--.

Col. 3, line 27, "aminO" should read --amino--.

Col. 3, line 51, "sceondary" should read --secondary--.

Col. 7, line 32, a period should be inserted after "evaporated".

Col. 7, line 49, "dicaboxylic" should read --dicarboxylic--.

Col. 7, line 50, "2-methyl" should begin a new line.

Col. 8, line 30, "100 ml." should read --1000 ml.--.

Col. 9, line 30, "1,3" should read --1.3--.

Col. 10, line 25, "is" should be deleted.

Col. 10, line 61, a period should be inserted after "compound".

Col. 11, line 13, "diethyl" should read --dimethyl--.

Col. 12, line 63, "z" should read --Z--.

Signed and Sealed this

Twelfth Day of October 1976

[SEAL]

Attest:

RUTH C. MASON
Attesting Officer

C. MARSHALL DANN
Commissioner of Patents and Trademarks